United States Patent
Ishida et al.

(10) Patent No.: US 7,622,615 B2
(45) Date of Patent: Nov. 24, 2009

(54) PROCESS FOR PRODUCING CYCLOALKANOL AND/OR CYCLOALKANONE

(75) Inventors: Hajime Ishida, Ehime (JP); Masashi Yokota, Ehime (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/100,524

(22) Filed: Apr. 10, 2008

(65) Prior Publication Data

US 2008/0255392 A1    Oct. 16, 2008

(30) Foreign Application Priority Data

Apr. 13, 2007    (JP) .............................. 2007-105834

(51) Int. Cl.
C07C 45/27 (2006.01)
C07C 35/08 (2006.01)
(52) U.S. Cl. ........................................ 568/357; 568/822
(58) Field of Classification Search ................. 568/357, 568/822
See application file for complete search history.

(56) References Cited

U.S. PATENT DOCUMENTS

| 4,103,827 A | 8/1978 | Kumazawa |
| 4,491,674 A | 1/1985 | Rieber et al. |
| 4,587,363 A | 5/1986 | Hartig et al. |
| 2004/0241059 A1 | 12/2004 | Seidlitz et al. |

FOREIGN PATENT DOCUMENTS

| EP | 1 741 694 A1 | 1/2007 |
| JP | 9-202742 A | 8/1997 |
| JP | 2002-249451 A | 9/2002 |
| JP | 2006-142300 A | 6/2006 |
| JP | 2006-159187 A | 6/2006 |
| WO | WO 01/36105 A1 | 5/2001 |

*Primary Examiner*—Sikarl A Witherspoon
(74) *Attorney, Agent, or Firm*—Sughrue Mion, PLLC

(57) ABSTRACT

There is provided a process with which the cycloalkane is oxidized so as to produce a cycloalkanol and/or a cycloalkanone with an improved conversion of the cycloalkane.

Such process includes the steps of supplying the oxygen-containing gas and a liquid including the cycloalkane into a bubble forming apparatus so as to prepare a gas-liquid mixture, and supplying such gas-liquid mixture into a reaction vessel.

12 Claims, No Drawings

PROCESS FOR PRODUCING CYCLOALKANOL AND/OR CYCLOALKANONE

BACKGROUND OF THE INVENTION

1. Field of the Invention

The present invention relates to a process for producing a cycloalkanol and/or a cycloalkanone by oxidizing a cycloalkane with an oxygen-containing gas.

2. Related Art

For the production of a cycloalkanol and/or a cycloalkanone by oxidizing a cycloalkane with an oxygen-containing gas, U.S. Pat. No. 4,587,363 discloses a process for supplying the oxygen-containing gas to a reaction system through a nozzle; Japanese Patent Kokai Publication No. H09-202742 discloses a process for supplying the oxygen-containing gas to a reaction system through a gas introducing tube; and Japanese Patent Kokai Publication No. 2002-249451 discloses a process for supplying the oxygen-containing gas to a reaction system through a filter which is attached to an end of a gas introducing tube.

SUMMARY OF THE INVENTION

The above mentioned processes are not always sufficient from a viewpoint of a conversion of the cycloalkane. It is, therefore, an object of the present invention to provide a process for oxidizing a cycloalkane so as to produce a cycloalkanol and/or a cycloalkanone (that is, at least one of the cycloalkanol and cycloalkane) with an improved conversion of the cycloalkane.

The present invention provides a process for producing a cycloalkanol and/or a cycloalkanone by oxidizing a cycloalkane with an oxygen-containing gas in a reaction vessel (or a reactor), which process comprising the steps of supplying the oxygen-containing gas and a liquid into a bubble forming apparatus so as to prepare a gas-liquid mixture, and supplying the gas-liquid mixture into the reaction vessel.

According to the present invention, the cycloalkane is converted with an improved conversion thereof to the cycloalkanol and/or the cycloalkanone.

DETAILED DESCRIPTION OF THE INVENTION

In the present invention, the cycloalkane is used as a raw material, which is oxidized with the oxygen-containing gas. As the cycloalkane for the raw material, for example the following compounds may be used: a mono-cyclic cycloalkane having no substituent on its ring such as cyclopropane, cyclobutane, cyclopentane, cyclohexane, cycloheptane, cyclooctane, cyclodecane and cyclooctadecane; and a polycyclic cycloalkane such as decalin, and adamantane. Such cycloalkanes may have a substituent(s) on its ring(s) such as a methylcyclopentane and a methylcyclohexane. Optionally, two or more above mentioned compounds may be used.

The oxygen-containing gas may, for example, be air or pure oxygen. Alternatively, air or pure oxygen may be diluted by an inert gas such as nitrogen, argon or helium. Further, oxygen rich air may be used which is produced by adding pure oxygen to air.

Oxidizing, that is, the oxidation reaction may be carried out without a catalyst, or under the presence of a catalyst such as a cobalt compound. As such a cobalt compound, a compound including a divalent or trivalent cobalt is usually used. Such cobalt compound may be in the form of for example an oxide, an organic acid salt, an inorganic acid salt, a halogenated compound, an alkoxide, or a complex such as an acetyl acetonate.

As the above mentioned cobalt compound, the following compounds are preferably exemplified: cobalt acetate, cobalt octanate, cobalt 2-ethylhexanate, cobalt naphtenate, cobalt stearate, cobalt acetylacetonate, cobalt chloride, and cobalt bromide.

An amount of the cobalt compound to be used is usually between 0.01 moles and 0.000000001 moles and preferably between 0.0001 moles and 0.0000001 moles per one mole of the cycloalkane.

In the present invention, the oxygen-containing gas and the liquid are supplied to a bubble forming apparatus so as to produce a gas-liquid mixture, which is supplied to the reaction vessel. Such gas-liquid mixture comprises bubbles, preferably fine bubbles, and more preferably very fine bubbles which are converted from the oxygen-containing gas in the bubble forming apparatus. The oxygen-containing gas is formed into the bubbles in the liquid in this way, and such bubbles are used for the oxidation reaction, so that cycloalkane can be oxidized with an improved conversion.

The bubble forming apparatus in the present invention is intended to mean an apparatus which prepares a gas-liquid mixture comprising bubbles, preferably fine bubbles, and particularly so-called micro-bubbles in the art using a gas and a liquid which are supplied to the apparatus. Such bubble forming apparatus may be the following: a swirling flow type bubble forming apparatus as disclosed in Japanese Patent Kokai Publication No. 2006-142300, a static mixer type bubble forming apparatus in which a gas and a liquid are mixed in a flow channel having structures such as baffles therein; and an ejector type bubble forming apparatus as disclosed in International Publication WO No. 01/036105 in which a liquid is ejected through a nozzle into a low pressure chamber, into which a gas is also introduced so that the gas-liquid mixture is prepared. The bubble forming apparatus which is preferably used in the present invention is of the ejector type apparatus.

To the bubble forming apparatus is supplied a liquid in addition to the oxygen-containing gas. As such liquid, the followings are exemplified: a liquid state cycloalkane to be oxidized; a solution in which a cycloalkane to be oxidized is dissolved; and a reaction liquid which is formed by the oxidation reaction of a cycloalkane which reaction is related to the present invention. Optionally, two or more of the above mentioned liquids may be used in combination. The liquid to be used in the present invention is preferably the cycloalkane itself and/or the reaction liquid.

A volume ratio of an amount of the liquid to an amount of the oxygen-containing gas (under the standard condition) to be supplied to the bubble forming apparatus is in the range usually between 0.01 and 10000, preferably between 0.1 and 2000, and more preferably between 1 and 1000.

In the present invention, the gas-liquid mixture prepared by the bubble forming apparatus is supplied to the reaction vessel or to the reaction vessel so as to carry out the oxidation reaction.

Preferably, such gas-liquid mixture is supplied to a reaction vessel, and particularly a liquid phase in the reaction vessel. In this way, the formed bubbles are more effectively used. The liquid phase herein used is intended to mean a liquid state cycloalkane, a solution prepared by dissolving a cycloalkane in a solvent, a reaction liquid which is prepared by the oxidation reaction related to the present invention or the like. The reaction liquid may comprise a catalyst such as the above mentioned cobalt compound which is dissolved and/or dispersed in the reaction liquid. In a particularly preferable embodiment, the bubble forming apparatus is placed in the reaction vessel such that the apparatus is submerged in the reaction liquid so that the gas-liquid mixture is directly supplied to the reaction vessel.

The reaction temperature is usually in the range between 0° C. and 200° C., preferably between 50° C. and 170° C., and more preferably between 80° C. and 150° C. The reaction pressure is usually in the range between 0.01 MPa and 10 MPa, and preferably between 0.1 MPa and 2 MPa. Optionally, a reaction solvent may be used, and for example a nitrile solvent (such as acetonitrile and benzonitrile), a carboxylic acid solvent (such as acetic acid, and propionic acid) or the like may be used as the solvent.

A post-processing which is carried out after the oxidation reaction is not particularly limited, and for example the reaction mixture which is prepared by the oxidation reaction is subjected to a filtration treatment, then a water washing treatment, and then a distillation treatment. When the reaction mixture contains a cycloalkyl hydroperoxide which corresponds to the cycloalkane as a raw material, such hydroperoxide may be converted to the aimed cycloalkane and/or cycloalkanone by means of an alkaline treatment, a reduction treatment or the like.

EXAMPLES

Examples of the present invention will hereinafter be described, but the present invention is not limited to such examples. It is noted that analysis of cyclohexane, cyclohexanone, cyclohexanol and cyclohexyl hydroperoxide was carried out using a gas chromatography, and a conversion of cyclohexane and selectivities of cyclohexanone, cyclohexanol and cyclohexyl hydroperoxide were calculated using thus obtained analysis data.

Example 1

With use of Ejector Type Bubble Forming Apparatus

Using a glass made autoclave having a volume of one liter as a reaction vessel, a bubble forming apparatus equipped with a gas supply tube and a liquid supply tube was placed in the autoclave. The apparatus was available from Aura-Tec under the trade name of O-Max, Type-I (ejector type). Cyclohexane (420 g) and cobalt (II) 2-ethylhexanate (0.35 mg) were charged into the autoclave, which was pressurized up to 0.93 MPa using nitrogen. Using a circulating pump, the liquid phase was discharged from of the reaction vessel at a flow rate of 1 liter/min. and supplied to the bubble forming apparatus while nitrogen was also supplied to the bubble forming apparatus at a flow rate of 100 Nml/min. so as to prepare a gas-liquid mixture, which was supplied to the liquid phase of the reaction vessel. In order to keep the pressure in the reaction vessel at 0.93 MPa, the gas phase in the reaction vessel was discharged to the outside of the reaction system, and the temperature of the liquid phase was heated to 140° C.

Then, the gas which was to be supplied to the gas phase was changed from nitrogen to air. An amount of the air to be supplied to the bubble forming apparatus was adjusted so that an oxygen concentration of the gas which was discharged out of the reaction system was kept not smaller than 0.4% by volume. The reaction was carried out for six hours.

Analysis of the liquid phase of the reaction vessel (or reaction liquid) showed that the conversion of cyclohexane was 11.0%, and the selectivities of cyclohexanone, cyclohexanol and cyclohexyl hydroxyperoxide were 38.1%, 30.6% and 11.0%, respectively. Further, the conversions at the time of two hours, four hours and six hours after the initiation of the reaction are also shown respectively in Table 1 below.

Comparative Example 1

Without use of Bubble Forming Apparatus

Without using a bubble forming apparatus, cyclohexane (420 g) and cobalt (II) 2-ethylhexanate (0.35 mg) were charged into a glass made autoclave having a volume of one liter as a reaction vessel and directly equipped with a liquid supply tube and a gas supply tube, and the reaction vessel was pressurized up to 0.93 MPa using nitrogen. Using a circulating pump, the liquid phase was discharged from the reaction vessel at a flow rate of 1 liter/min. and supplied again to the liquid phase of the reaction vessel through the liquid supply tube. Nitrogen was directly supplied to the liquid phase of the reaction vessel through the gas supply tube at a flow rate of 100 Nml/min. and the gas phase of the reaction vessel was discharged to the outside of the reaction system so as to keep the pressure in the reaction vessel at 0.93 MPa. The temperature of the liquid phase was heated to 140° C.

Then, the gas which was to be supplied to the gas phase was changed from nitrogen to air. An amount of the air to be supplied was adjusted so that an oxygen concentration of the gas which was discharged out of the reaction system was kept not smaller than 0.4% by volume. The reaction was carried out for six hours.

Analysis of the liquid phase of the reaction vessel showed that the conversion of cyclohexane was 2.4%, and the selectivities of cyclohexanone, cyclohexanol and cyclohexyl hydroxyperoxide were 43.8%, 31.5% and 17.8%, respectively. Further, the conversions at the time of two hours, four hours and six hours after the initiation of the reaction are also shown respectively in Table 1 below.

Comparative Example 2

With use of Sintered Filter

Cyclohexane (420 g) and cobalt (II) 2-ethylhexanate (0.35 mg) were charged into a glass made autoclave as a reaction vessel having a volume of one liter was used which was equipped with a liquid supply tube and a gas supply tube having a sintered filter (of which average pore size was 90

μm) at its end. The reaction vessel was pressurized up to 0.93 MPa using nitrogen. Using a circulating pump, the liquid phase was discharged from the reaction vessel at a flow rate of 1 liter/min. and supplied again to the liquid phase of the reaction vessel through the liquid supply tube. Nitrogen was supplied to the liquid phase of the reaction vessel from the gas supply tube through the sintered filter at a flow rate of 100 Nml/min. and the gas phase of the reaction vessel was discharged to the outside of the reaction system so as to keep the pressure in the reaction vessel at 0.93 MPa. The temperature of the liquid phase was heated to 140° C.

Then, the gas which is to be supplied to the gas phase was changed from nitrogen to air. An amount of the air to be supplied was adjusted so that an oxygen concentration of the gas which was discharged out of the reaction system was kept not smaller than 0.4% by volume The reaction was carried out for six hours.

Analysis of the liquid phase of the reaction vessel showed that the conversion of cyclohexane was 5.9%, and the selectivities of cyclohexanone, cyclohexanol and cyclohexyl hydroxyperoxide were 40.9%, 31.5% and 13.5%, respectively. Further, the conversions at the time of two hours, four hours and six hours after the initiation of the reaction are also shown respectively in Table 1 below.

TABLE 1

| | | Example 1 | Comparative Example 1 | Comparative Example 2 |
|---|---|---|---|---|
| gas supply manner | | with ejector type bubble forming apparatus | without specific gas supply manner (i.e. direct injection through gas supply tube) | with sintered filter |
| Conversion (%) | after 2 hours | 1.7 | 1.1 | 1.8 |
| | after 4 hours | 6.5 | 1.6 | 3.6 |
| | after 6 hours | 11.0 | 2.4 | 5.9 |

Example 2

With use of Ejector Type Bubble Forming Apparatus

Cobalt (II) 2-ethylhexanate (2.25 mg) was dissolved into cyclohexane (2700 g) so as to obtain a solution (A).

Using a glass made autoclave having a volume of one liter as a reaction vessel, a bubble forming apparatus equipped with a gas supply tube and a liquid supply tube was placed in the autoclave. The apparatus was available from Aura-Tec under the trade name of O-Max, Type-I (ejector type). The above solution (A) (300 g) was charged into the reaction vessel, which was pressurized up to 0.93 MPa using nitrogen. Using a circulating pump, the liquid phase was discharged from of the reaction vessel at a flow rate of 1 liter/min. and supplied to the bubble forming apparatus while nitrogen was also supplied to the bubble forming apparatus at a flow rate of 100 Nml/min. so as to prepare a gas-liquid mixture, which was supplied to the liquid phase of the reaction vessel. In order to keep the pressure of the reaction vessel at 0.93 MPa, a gas was discharged to the outside in the reaction system, and the temperature of the liquid phase was heated to 140° C.

Then, the gas which was to be supplied to the bubble forming apparatus was changed to 200 Nml/min. of nitrogen and 200 Nml/min. of air. Continuing the circulation of the liquid phase in the reaction vessel and the gas supply, the solution (A) was additionally supplied directly to the liquid phase of the reaction vessel at a flow rate of 5 g/min. while the liquid phase was discharged out of the reaction vessel so as to carry out the continuous reaction with keeping a constant amount of the liquid phase in the reaction vessel. A residence time of the liquid phase in the reaction vessel during the continuous reaction was 60 minutes.

Analysis of the liquid phase in the reaction vessel at the time of six hours after the initiation of the continuous reaction showed that the conversion of cyclohexane was 2.8%, and the selectivities of cyclohexanone, cyclohexanol and cyclohexyl hydroxyperoxide were 36.7%, 27.9% and 22.7%, respectively. Further, the conversion of six hours after the initiation of the reaction is shown also in Table 2 below.

Example 3

With use of Ejector Type Bubble Forming Apparatus

The above described Example 2 was repeated except that the flow rate of the solution (A) to be additionally supplied to the reaction vessel was changed to 3.8 g/min. The residence time of the liquid phase in this reaction was 80 minutes.

Analysis of the liquid phase in the reaction vessel at the time of eight hours after the initiation of the continuous reaction showed that the conversion of cyclohexane was 4.0%, and the selectivities of cyclohexanone, cyclohexanol and cyclohexyl hydroxyperoxide were 39.0%, 30.0% and 16.7%, respectively. Further, the conversion of eight hours after the initiation of the reaction is shown also in Table 2 below.

Example 4

With use of Ejector Type Bubble Forming Apparatus

The above described Example 2 was repeated except that the flow rate of the solution (A) to be additionally supplied to the reaction vessel was changed to 3.0 g/min. The residence time of the liquid phase in this reaction was 100 minutes.

Analysis of the liquid phase in the reaction vessel at the time of ten hours after the initiation of the continuous reaction showed that the conversion of cyclohexane was 4.9%, and the selectivities of cyclohexanone, cyclohexanol and cyclohexyl hydroxyperoxide were 38.3%, 28.7% and 14.6%, respectively. Further, the conversion of two hours, ten hours after the initiation of the reaction is shown also in Table 2 below.

Comparative Example 3

Without use of Bubble Forming Apparatus

Without using a bubble forming apparatus, the above described solution (A) (300 g) was charged into a glass made autoclave having a volume of one liter as a reaction vessel and equipped with a liquid supply tube and a gas supply tube, and the reaction vessel was pressurized up to 0.93 MPa using nitrogen. Using a circulating pump, the liquid phase was discharged from of the reaction vessel at a flow rate of 1 liter/min. and supplied again to the liquid phase of the reaction vessel through the liquid supply tube. Nitrogen was supplied to the liquid phase of the reaction vessel through the gas supply tube at a flow rate of 100 Nml/min and discharged to the outside of the reaction system so as to keep the pressure of the reaction vessel at 0.93 MPa. The temperature of the liquid phase was heated to 140° C.

Then, the gas which was to be supplied through the gas supply tube was changed to 200 Nml/min. of nitrogen and 200 Nml/min. of air. Then, continuing the circulation of the liquid phase in the reaction vessel and the gas supply, the solution (A) was additionally supplied directly to the reaction vessel at a flow rate of 5 g/min. while the liquid phase was discharged out of the reaction vessel so as to carry out the continuous reaction with keeping a constant amount of the liquid phase in the reaction vessel. A residence time of the liquid phase in the reaction vessel during the continuous reaction was 60 minutes.

Analysis of the liquid phase in the reaction vessel at the time of six hours after the initiation of the continuous reaction showed that the conversion of cyclohexane was 1.9%, and the selectivities of cyclohexanone, cyclohexanol and cyclohexyl hydroxyperoxide were 35.6%, 22.2% and 31.6%, respectively. Further, the conversion of six hours after the initiation of the reaction is shown also in Table 2 below.

Comparative Example 4

Without use of Bubble Forming Apparatus

The above described Comparative Example 3 was repeated except that the flow rate of the solution (A) to be additionally supplied to the reaction vessel was changed to 3.8 g/min. The residence time of the liquid phase in this reaction was 80 minutes.

Analysis of the liquid phase in the reaction vessel at the time of eight hours after the initiation of the continuous reaction showed that the conversion of cyclohexane was 2.4%, and the selectivities of cyclohexanone, cyclohexanol and cyclohexyl hydroxyperoxide were 40.1%, 27.1% and 21.5%, respectively. Further, the conversion of eight hours after the initiation of the reaction is shown also in Table 2 below.

Comparative Example 5

Without use of Bubble Forming Apparatus

The above described Comparative Example 3 was repeated except that the flow rate of the solution (A) to be additionally supplied to the reaction vessel was changed to 3.0 g/min. The residence time of the liquid phase in this reaction was 100 minutes.

Analysis of the liquid phase in the reaction vessel at the time of ten hours after the initiation of the continuous reaction showed that the conversion of cyclohexane was 3.1%, and the selectivities of cyclohexanone, cyclohexanol and cyclohexyl hydroxyperoxide were 42.1%, 30.9% and 13.7%, respectively. Further, the conversion of ten hours after the initiation of the reaction is shown also in Table 2 below.

Comparative Example 6

Without use of Bubble Forming Apparatus

The above described Comparative Example 3 was repeated except that the flow rate of the solution (A) to be additionally supplied to the reaction vessel was changed to 2.0 g/min. The residence time of the liquid phase in this reaction was 150 minutes.

Analysis of the liquid phase in the reaction vessel at the time of fifteen hours after the initiation of the continuous reaction showed that the conversion of cyclohexane was 5.0%, and the selectivities of cyclohexanone, cyclohexanol and cyclohexyl hydroxyperoxide were 42.0%, 34.0% and 5.7%, respectively. Further, the conversion of fifteen hours after the initiation of the reaction is shown also in Table 2 below.

TABLE 2

|  | Example 2 | Example 3 | Example 4 | Comparative Example 3 | Comparative Example 4 | Comparative Example 5 | Comparative Example 6 |
| --- | --- | --- | --- | --- | --- | --- | --- |
| gas supply manner | with ejector type bubble forming apparatus | | | without specific gas supply manner (i.e. direct injection through gas supply tube) | | | |
| residence time (min.) | 60 | 80 | 100 | 60 | 80 | 100 | 150 |
| reaction period (hrs) | 6 | 8 | 10 | 6 | 8 | 10 | 15 |
| conversion (%) | 2.8 | 4.0 | 4.9 | 1.9 | 2.4 | 3.1 | 5.0 |

INDUSTRIAL APPLICABILITY

According to the present invention, the cycloalkane is oxidized so as to produce the cycloalkanol and/or the cycloalkanone with the improved conversion of the cycloalkane.

What is claimed is:

1. A process for producing a cycloalkanol and/or a cycloalkanone by oxidizing a cycloalkane with an oxygen-containing gas in a reaction vessel, which process comprising the steps of supplying the oxygen-containing gas and a liquid into a bubble forming apparatus so as to prepare a gas-liquid mixture, and supplying the gas-liquid mixture into the reaction vessel.

2. The process according to claim 1 wherein the step of supplying the gas-liquid mixture into the reaction vessel is carried out by supplying the mixture into a liquid phase in the reaction vessel.

3. The process according to claim 1 wherein the bubble forming apparatus is an ejector type bubble forming apparatus.

4. The process according to claim 2 wherein the bubble forming apparatus is an ejector type bubble forming apparatus.

5. The process according to claim 3 wherein the liquid is the cycloalkane and/or a reaction liquid formed by the oxidizing the cycloalkane.

6. The process according to claim 4 wherein the liquid is the cycloalkane and/or a reaction liquid formed by the oxidizing the cycloalkane.

7. The process according to claim 3 wherein the cycloalkane comprises cyclohexane.

8. The process according to claim 4 wherein the cycloalkane comprises cyclohexane.

9. The process according to claim 5 wherein the cycloalkane comprises cyclohexane.

10. The process according to claim 6 wherein the cycloalkane comprises cyclohexane.

11. The process according to claim 1 wherein the bubble forming apparatus is a micro-bubble forming apparatus.

12. The process according to claim 2 wherein the bubble forming apparatus is a micro-bubble forming apparatus.

* * * * *